US012751781B2

(12) United States Patent
Bar

(10) Patent No.: US 12,751,781 B2
(45) Date of Patent: Oct. 6, 2026

(54) TWO-TOOL ANATOMY STABILIZATION

(71) Applicant: LEM Surgical AG, Bern (CH)

(72) Inventor: Yossi Bar, Muri bei Bern (CH)

(73) Assignee: LEM Surgical AG, Bern (CH)

( * ) Notice: Subject to any disclaimer, the term of this patent is extended or adjusted under 35 U.S.C. 154(b) by 158 days.

(21) Appl. No.: 18/767,761

(22) Filed: Jul. 9, 2024

(65) Prior Publication Data

US 2024/0358460 A1 Oct. 31, 2024

Related U.S. Application Data

(63) Continuation-in-part of application No. 18/734,249, filed on Jun. 5, 2024, which is a continuation of
(Continued)

(51) Int. Cl.
*A61B 34/32* (2016.01)
*A61B 34/00* (2016.01)
(Continued)

(52) U.S. Cl.
CPC .............. *A61B 34/32* (2016.02); *A61B 34/25* (2016.02); *A61B 34/30* (2016.02); *A61B 50/13* (2016.02);
(Continued)

(58) Field of Classification Search
CPC ......... A61B 34/32; A61B 34/35; A61B 34/25; A61B 2034/252; A61B 34/30; A61B 2034/303; A61B 50/13; A61B 90/39; A61B 90/50; A61B 2034/2055; A61B 2090/3966; B25J 9/1682
(Continued)

(56) References Cited

U.S. PATENT DOCUMENTS

| | | | |
|---|---|---|---|
| 6,699,177 | B1 | 3/2004 | Wang et al. |
| 9,125,680 | B2 | 9/2015 | Kostrzewski et al. |

(Continued)

FOREIGN PATENT DOCUMENTS

| | | | |
|---|---|---|---|
| CN | 109549706 A | 4/2019 | |
| CN | 110013313 A | 7/2019 | |

(Continued)

OTHER PUBLICATIONS

PCT/EP2025/069284 International Search Report and Written Opinion dated Oct. 9, 2025.

(Continued)

*Primary Examiner* — Aaron F Roane
(74) *Attorney, Agent, or Firm* — Wilson Sonsini Goodrich & Rosati

(57) ABSTRACT

Robotic surgical procedures are successively performed on a patient's bony anatomy by engaging the patient's bony anatomy with a first tool or implant coupled to a first surgical robotic arm to perform a first procedure. A second tool or implant coupled to a second surgical robotic arm is then used to perform a second procedure while the first surgical robotic arm and the first tool or implant remain engaged with the patient's bony anatomy to stabilize the bony anatomy while the second procedure is being performed with the second surgical robotic arm and second tool or implant.

23 Claims, 9 Drawing Sheets

Related U.S. Application Data application No. 18/217,595, filed on Jul. 2, 2023, now Pat. No. 12,029,511, which is a continuation of application No. PCT/IB2022/052297, filed on Mar. 14, 2022.

(60) Provisional application No. 63/253,533, filed on Oct. 7, 2021.

(51) Int. Cl.

| | |
|---|---|
| ***A61B 34/30*** | (2016.01) |
| ***A61B 50/13*** | (2016.01) |
| ***A61B 90/00*** | (2016.01) |
| ***A61B 90/50*** | (2016.01) |
| ***B25J 9/16*** | (2006.01) |
| *A61B 34/20* | (2016.01) |

(52) U.S. Cl.
CPC .............. *A61B 90/39* (2016.02); *A61B 90/50* (2016.02); *B25J 9/1682* (2013.01); *A61B 2034/2055* (2016.02); *A61B 2090/3966* (2016.02)

(58) Field of Classification Search
USPC .............................................................. 606/1
See application file for complete search history.

(56) References Cited

U.S. PATENT DOCUMENTS

| | | | | |
|---|---|---|---|---|
| 10,512,509 | B2 | 12/2019 | Bowling et al. | |
| 10,716,958 | B2 | 7/2020 | Neff | |
| 11,638,618 | B2 | 5/2023 | Schuh et al. | |
| 12,029,511 | B2 | 7/2024 | Bar | |
| 12,114,946 | B2 | 10/2024 | Bar et al. | |
| 2003/0074732 | A1 | 4/2003 | Hanson et al. | |
| 2005/0206107 | A1 | 9/2005 | Schubert et al. | |
| 2010/0286712 | A1 | 11/2010 | Won et al. | |
| 2015/0193101 | A1 | 7/2015 | Mannon et al. | |
| 2015/0366624 | A1 | 12/2015 | Kostrzewski et al. | |
| 2018/0193101 | A1 | 7/2018 | Hashimoto | |
| 2018/0360550 | A1 | 12/2018 | Nakanishi | |
| 2018/0362060 | A1 | 12/2018 | Schaller et al. | |
| 2019/0008598 | A1 | 1/2019 | Frimer et al. | |
| 2020/0078097 | A1 | 3/2020 | Gregerson et al. | |
| 2020/0268452 | A1* | 8/2020 | Rezach | A61B 34/30 |
| 2020/0281788 | A1 | 9/2020 | Lim et al. | |
| 2020/0405432 | A1 | 12/2020 | Timm et al. | |
| 2021/0045819 | A1 | 2/2021 | Castillo et al. | |
| 2021/0060767 | A1 | 3/2021 | Guerrera et al. | |
| 2021/0186615 | A1 | 6/2021 | Shmayahu et al. | |
| 2021/0338348 | A1 | 11/2021 | Zehavi et al. | |
| 2022/0079687 | A1 | 3/2022 | Sexson et al. | |
| 2022/0160445 | A1 | 5/2022 | Meglan et al. | |
| 2022/0168048 | A1 | 6/2022 | Shoham et al. | |
| 2022/0241032 | A1 | 8/2022 | Zucker et al. | |
| 2022/0346882 | A1 | 11/2022 | Zehavi et al. | |
| 2022/0395342 | A1* | 12/2022 | Weiss | A61B 6/4458 |
| 2023/0380916 | A1 | 11/2023 | Bar | |
| 2023/0414431 | A1 | 12/2023 | Lim et al. | |
| 2024/0164854 | A1 | 5/2024 | Bar | |
| 2024/0206973 | A1 | 6/2024 | Charest et al. | |
| 2024/0261046 | A1 | 8/2024 | Bar | |
| 2024/0268919 | A1 | 8/2024 | Bar | |
| 2024/0341877 | A1 | 10/2024 | Bar | |
| 2024/0366320 | A1 | 11/2024 | Bar | |
| 2024/0423728 | A1 | 12/2024 | Bar | |
| 2024/0423730 | A1 | 12/2024 | Bar | |
| 2024/0423731 | A1 | 12/2024 | Bar | |
| 2025/0032208 | A1 | 1/2025 | Bar | |
| 2025/0049520 | A1 | 2/2025 | Bar et al. | |
| 2025/0114158 | A1 | 4/2025 | Bar | |
| 2025/0143813 | A1 | 5/2025 | Bar | |
| 2025/0235206 | A1 | 7/2025 | Bar | |
| 2025/0345127 | A1 | 11/2025 | Bar et al. | |
| 2025/0345134 | A1 | 11/2025 | Bar et al. | |
| 2025/0352289 | A1 | 11/2025 | Bar | |
| 2026/0033901 | A1 | 2/2026 | Bar | |
| 2026/0047900 | A1 | 2/2026 | Bar et al. | |

FOREIGN PATENT DOCUMENTS

| | | | |
|---|---|---|---|
| CN | 111700684 | A | 9/2020 |
| JP | 2017104452 | A | 6/2017 |
| WO | WO-2018222470 | A1 | 12/2018 |
| WO | WO-2018236594 | A1 | 12/2018 |
| WO | WO-2020079596 | A1 | 4/2020 |
| WO | WO-2022044009 | A1 | 3/2022 |
| WO | WO-2022069993 | A1 | 4/2022 |
| WO | WO-2022195460 | A1 | 9/2022 |
| WO | WO-2023067415 | A1 | 4/2023 |
| WO | WO-2023118984 | A1 | 6/2023 |
| WO | WO-2023118985 | A1 | 6/2023 |
| WO | WO-2023144602 | A1 | 8/2023 |
| WO | WO-2023152561 | A1 | 8/2023 |
| WO | WO-2023223215 | A1 | 11/2023 |
| WO | WO-2023237922 | A1 | 12/2023 |
| WO | WO-2023248005 | A1 | 12/2023 |
| WO | WO-2024089473 | A1 | 5/2024 |
| WO | WO-2024160875 | A1 | 8/2024 |
| WO | WO-2024160896 | A1 | 8/2024 |
| WO | WO-2024165397 | A1 | 8/2024 |
| WO | WO-2025008416 | A1 | 1/2025 |
| WO | WO-2025036864 | A1 | 2/2025 |
| WO | WO-2025038127 | A1 | 2/2025 |
| WO | WO-2025108905 | A1 | 5/2025 |
| WO | WO-2025119761 | A1 | 6/2025 |
| WO | WO-2025125379 | A1 | 6/2025 |
| WO | WO-2025195791 | A1 | 9/2025 |
| WO | WO-2025195902 | A1 | 9/2025 |
| WO | WO-2025209993 | | 10/2025 |
| WO | WO-2025257316 | A1 | 12/2025 |
| WO | WO-2026012973 | A1 | 1/2026 |
| WO | WO-2026012978 | A1 | 1/2026 |
| WO | WO-2026062107 | | 3/2026 |
| WO | WO-2026062108 | | 3/2026 |

OTHER PUBLICATIONS

PCT/EP2025/069291 International Search Report and Written Opinion dated Oct. 14, 2025.
PCT/IB2022/052297 International Search Report and Written Opinion dated Jun. 14, 2022.
U.S. Appl. No. 18/217,595 Notice of Allowance dated Mar. 21, 2024.
U.S. Appl. No. 18/217,595 Office Action dated Dec. 14, 2023.
U.S. Appl. No. 18/217,595 Office Action dated Feb. 1, 2024.
U.S. Appl. No. 18/217,595 Office Action dated Sep. 28, 2023.
U.S. Appl. No. 18/734,249 Office Action dated Mar. 5, 2026.
U.S. Appl. No. 18/767,753 Office Action dated Mar. 12, 2026.
U.S. Appl. No. 18/783,197 Office Action dated Mar. 12, 2026.

* cited by examiner

TWO-TOOL ANATOMY STABILIZATION

CROSS-REFERENCE TO RELATED APPLICATIONS

This application is a continuation-in-part of U.S. application Ser. No. 18/734,249, filed on Jun. 5, 2024, which is a continuation of U.S. application Ser. No. 18/217,595, filed on Jul. 2, 2023, now issued as U.S. Pat. No. 12,029,511, issued on Jun. 19, 2024, which is a continuation of PCT application no. PCT/IB2022/052297, filed on Mar. 14, 2022, which claims the benefit of U.S. provisional application No. 63/161,716, filed on Mar. 16, 2021, and U.S. provisional application No. 63/253,533 filed on Oct. 7, 2021, the full disclosures of each of which are incorporated herein by reference.

BACKGROUND

1. Field

The disclosed technology relates generally to medical devices and methods for their use. More particularly, the technology relates to surgical robots and robotic surgical procedures performed using multiple surgical tools in a plurality of sequential surgical steps.

Surgical robots can take a variety of forms. One common approach is to mount multiple robotic surgical arms directly on a surgical table. A base of each arm will typically be fixed to the table, and the table and robotic system will share a common surgical coordinate space. In another approach, multiple robotic surgical arms are mounted on one or more mobile carts that can be moved in and out proximity with the surgical table. The multiple robotic surgical arms can be registered in various ways to be manipulated in a coordinated fashion in order to perform the sequential steps necessary to carry out a variety of surgical procedures in a common surgical coordinate space.

Control of the multiple robotic surgical arms can be performed kinematically, using real-time image-based navigation, or a combination of both approaches. Put very simply, kinematic positioning calculates the position of a surgical tool in the surgical robotic coordinate space based upon a known, fixed position of the robotic arm base in the robotic coordinate space and the dimensions and angulations of the robotic arm segments which are controlled by the robotic controller and which vary over time. As kinematic positioning is often performed without the benefit of optical navigation backup, it is very important that the patient's anatomy remain fixed within the robotic surgical coordinate space over the course of a procedure so that the kinematically positioned surgical tool is properly positioned relative to the patient anatomy.

Shifting of patient anatomy during a procedure can be a particular challenge when performing spinal and other robotic orthopedic procedures. Drilling, grinding, distraction, inserting screws and implants, and the like, can require the application of significant forces which can shift the position of the bony anatomy during the procedure. Such changes in position can make tool navigation problematic particularly when relying primarily or solely on kinematic navigation.

In robotic spine surgery, maintaining tool position accuracy when moving from vertebra to vertebra along the spine. the relative motion between one vertebra and another. Drilling or otherwise engaging one vertebra can physically shift and within the surgical robotic coordinate space and relative to the other vertebrae in the spine, complicating kinematic and other positioning of the tools being manipulated by the surgical tools being used in the procedure.

There is thus a need for robotic surgical systems and methods which can stabilize the position of a patient's bony anatomy during the performance of orthopedic procures, including but not limited to spinal procedures. It would be particularly useful to provide methods and protocols that can be implemented by surgical robotic controllers with minimal or no changes in the mechanical components of the surgical robot. At least some if these objectives will be met by the technologies disclosed herein.

2. Background Art

Commonly owned publications and applications describing surgical robots and tools include PCT application nos.: PCT/IB2022/052297 (published as WO2022/195460); PCT/IB2022/058986 (published as WO2023/067415); PCT/IB2022/058972 (published as WO2023/118984); PCT/IB2022/058982 (published as WO2023/118985); PCT/IB2022/058978 (published as WO2023/144602); PCT/IB2022/058980 (published as WO2023/152561); PCT/IB2023/055047 (published as WO2023/223215); PCT/IB2022/058988 (published as WO2023/237922); PCT/IB2023/055439; PCT/IB2023/055662; PCT/EP2024/052338; PCT/IB2023/055663; PCT/EP2024/052338; PCT/IB2023/056911; PCT/EP2024/052353; and U.S. provisional application Nos. 63/532,753, 63/568,102, 63/578,395; 63/606,001; 63/609,490; 63/615,076; 63/634,161, the full disclosures of each of which are incorporated herein by reference.

SUMMARY

In a first aspect, the technologies disclosed herein provide a robotic method for performing successive robotic surgical procedures on a patient's bony anatomy. The term "procedure" as used herein designates any single step or operation that is performed by a surgical robot on a patient anatomy, typically a bony anatomy such as the patient's spine, in a robotic surgery. Exemplary steps or operations include but are not limited to drilling, grinding, milling, distraction, inserting screws and implants, and the like. Other target bony anatomies include hips, knees, ankles, and other robotic procedures include prosthetic implantations.

The methods herein comprise engaging the patient's bony anatomy with a first tool or a first implant coupled to a first surgical robotic arm to perform a first procedure and engaging the patient's bony anatomy with a second tool or a second implant coupled to a second surgical robotic arm to perform a second procedure. The first surgical robotic arm and the first tool or the first implant remain engaged with the patient's bony anatomy to stabilize the bony anatomy while the second procedure is being performed with the second surgical robotic arm and the second tool or the second implant.

The first tool or implant that is stabilizing the bony or other anatomy will often penetrate the anatomy to provide a strong connection that allows the surgical robotic arm, when immobilized, to inhibit the anatomy from moving as the second procedure is being performed on the target and/or an adjacent anatomy. Penetration can be made by drill bits, screws, fasteners, implants, and the like which will remain attached or otherwise mechanically coupled to the supporting surgical robotic arm. In other instances, the stabilizing element can engage but not penetrate the target bony anatomy, for example, cannulas and other tools have blunt tips which engage and stabilize but which do not penetrate the anatomy. In still other instances, the stabilizing tools can be configured to grasp and release the target anatomy without penetration.

These method steps are typically implemented using a robotic surgical controller which is part of the surgical robot. In most cases the surgical robot arms and/or the surgical tools will be operated by the surgeon using an interface such as a display screen on the surgical robot, a remote workstation including optical and/or other sensor-based imaging and tracking capabilities, or the like. In other instances, control of the surgical robot arms and/or the surgical tools may be performed partly or entirely automatically by the surgical robotic controller.

In some instances, the first procedure comprises drilling.

In some instances, the first procedure comprises placing an implant.

In some instances, the first procedure comprises drilling and placing a first pedicle screw at a first location in the patient's bony anatomy. For example, the second procedure may comprise drilling and placing a second pedicle screw at a second location in the patient's bony anatomy. In such cases, the first and second locations may be located in the same vertebra. In some cases, the first and second locations may be located in separate vertebra.

In an exemplary method, additional pedicle screws are placed in a zig-zag pattern while alternating stabilization with the first and second robotic arms.

In a second aspect, the technologies disclosed herein provide a robotic surgical system comprising a chassis, a first surgical robotic arm, a second surgical robotic arm, and a surgical robotic controller. The first surgical robotic arm is disposed on the chassis and is configured to hold a first surgical tool or implant. The second surgical robotic arm is also disposed on the chassis and is configured to hold a second surgical tool or implant. The surgical robotic controller is configured to control motion of the first and second surgical arms and the first and second tools or implants so that the first surgical robotic arm and the first tool or the first implant perform a first procedure on a first location on the patient's bony anatomy and remain engaged with the patient's bony anatomy after the first procedure is completed to stabilize the bony anatomy while a second procedure is being performed with the second surgical robotic arm and the second tool or the second implant.

In some instances, the surgical robotic controller is further configured to control motion of the first arm and the first tool or implant to penetrate the first tool or implant into the bony anatomy and to cause the first tool or implant to remain penetrated in the patient's bony anatomy to stabilize the bony anatomy while the second procedure is being performed.

In some instances, the first procedure comprises drilling.

In some instances, the first procedure comprises placing an implant.

In some instances, the first procedure comprises drilling and placing a first pedicle screw at a first location in the patient's bony anatomy. For example, the second procedure may comprise drilling and placing a second pedicle screw at a second location in the patient's bony anatomy where the first and second locations may be located in the same or in successive vertebra.

In some instances, the surgical robotic controller is further configured to place additional pedicle screws in a zig-zag pattern while alternating stabilization with the first and second robotic arms.

In a third aspect, the technologies disclosed herein provide a robotic surgical system comprising a chassis, a first surgical robotic arm, a second surgical robotic arm, and a surgical robotic controller. The first surgical robotic arm may be disposed on the chassis and may be configured to hold a first surgical tool or implant. The second surgical robotic arm may be disposed on the chassis and may be configured to hold a second surgical tool or implant. The surgical robotic controller will typically be configured to control motion of the first and second surgical arms and the first and second tools or implants so that the first surgical robotic arm and the first tool or the first implant can perform a first procedure at a first location on the patient's bony anatomy and remain engaged with the patient's bony anatomy after the first procedure is completed to stabilize the bony anatomy while a second procedure is being performed.

Control of the multiple robotic surgical arms may be performed kinematically, using real-time image-based navigation, or using a combination of both approaches. Kinematic positioning calculates the position of a surgical tool in the surgical robotic coordinate space based upon a known, fixed position of the robotic arm base in the robotic coordinate space and the dimensions and angulations of the robotic arm segments which are controlled by the robotic controller, and which vary over time. In contrast, navigation based upon imaging will typically rely on registering a pre-operative image of the patient's anatomy, usually a three-dimensional CT scan, with the robot's coordinate space.

In specific instances, the surgical robotic controller may be further configured to control motion of the first arm and the first tool or implant to cause penetration of the first tool or implant into the bony anatomy and to cause the first tool or implant to remain penetrated in the patient's bony anatomy to stabilize the bony anatomy while the second procedure is being performed.

In some instances, the first procedure may comprise drilling.

In some instances, the first procedure may comprise placing an implant.

In some instances, the first procedure may comprise drilling and placing a first pedicle screw at a first location in the patient's bony anatomy. In such instances, the second procedure may comprise drilling and placing a second pedicle screw at a second location in the patient's bony anatomy where the first and second locations may be in the same vertebra or may be in separate vertebra.

In some instances, the surgical robotic controller may be further configured to control motion of the first and second surgical arms and tools or implants to implant pedicle screws in a zig-zag pattern while alternating stabilization with the first and second robotic arms.

Leaving a robotic arm connected to a drill, screw or other implant, which remains rigidly connected to a vertebra or other bony anatomy, can act as a stabilizer for the next operative step in adjacent bony anatomy, for example vertebra/pedicle drilling in either in the same vertebra or an adjacent vertebra (above or below). The system can then continue drilling and placing screws in a "Zigzag" patten (left and right and up and down) i.e., left drilling while stabilized by a right grip and vice versa.

The robotic arms of the disclosed technology will preferably be short, strong and rigidly connected to the same rigid platform (e.g., the cart), allowing the surgical robotic arms to hold the implants which are rigidly inserted to the pedicles of the vertebrae (for example) from both sides and manipulate the vertebrae in relation to each other. This technique can also be used to manipulate two or more vertebrae (e.g., indirect decompression, compression, distraction etc.) and even the entire spine. Having two or more arms located one in front of the other can enable them to distract two vertebrae by several millimeters and keep this distraction constant and safe while the surgeon is performing delicate surgical tasks between the vertebrae (e.g. disc removal, decompression etc.).

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

With reference now to the figures and several representative embodiments of the described technology, the following detailed description is provided.

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" in some cases refers to an amount that is approximately the stated amount.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Figure 1:
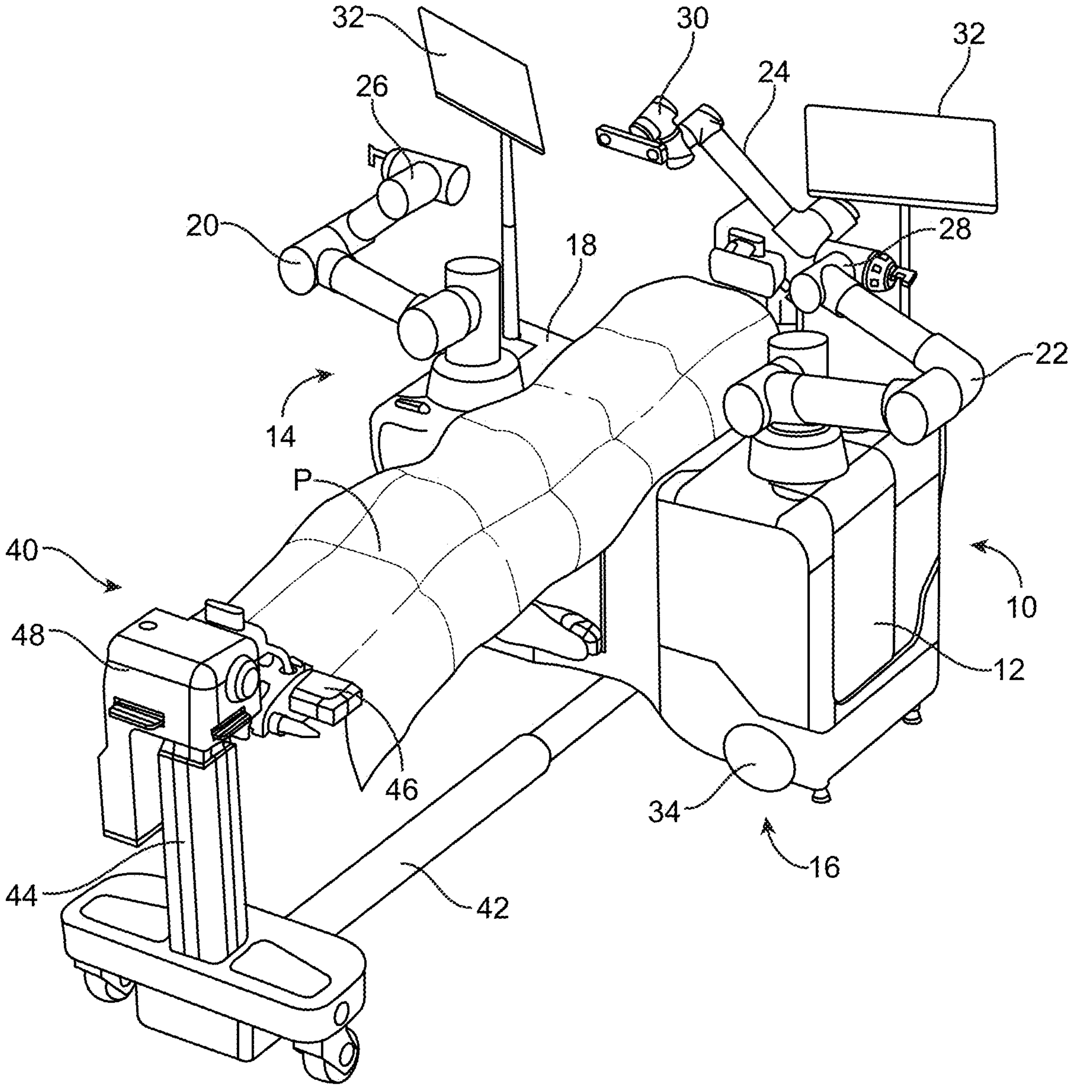
FIG. 1 is a perspective view of a mobile surgical robotic cart of the type suitable for performing the methods of the disclosed technology shown positioned beneath a surgical table with surgical robotic arms deployed over a draped patient, in accordance with some embodiments.

An exemplary robotic surgical system 10 which is suitable for performing in the methods described and claimed herein is shown in FIG. 1. The robotic surgical system 10 can comprise a chassis 12, typically a single, rigid frame which provides a base or platform for three robotic arms 20, 22 and 24 that are placed relatively far apart on opposite longitudinal ends 14 and 16 of an upper surface 18 of the chassis 12, typically approximately one meter apart, thus allowing for desirable attributes such as reachability, maneuverability, and an ability to apply significant force. In the illustrated embodiment, robotic surgical arms 20 and 22 are on the first end 14 of the chassis 12 and robotic surgical arm 22 is on the second end 16 of the chassis. The chassis can be mobile, e.g. being in the form of a mobile cart as described in commonly owned PCT/IB2022/052297 (published as WO2022/195460), previously incorporated herein by reference. In other embodiments and implementations, the surgical arms 20, 22 and 24 can be mounted on a base or other structure of a surgical table. For performing tool alignment in accordance with the disclosed technology, it necessary only that the robotic surgical arms be located on a stable platform that allows the arms to be moved kinematically or otherwise within a common robotic coordinate system under the control of a surgical robotic controller, typically an on-board controller have a user interface, such as display screen 32.

The single, rigid chassis of the disclosed technology can include a single mobile cart, as disclosed for example in commonly owned PCT/IB2022/052297 (published as WO2022/195460), the full disclosure of which has been previously incorporated herein by reference. In other instances, however, the single, rigid chassis may comprise separate modules, platforms, or components, that are assembled at or near the surgical table, as described for example in commonly owned PCT application no. PCT/EP2024/052353, entitled Integrated Multi-Arm Mobile Surgical Robotic System, filed on Jan. 29, 2024, the full disclosure of which is incorporated herein by reference. The only requirement of the single, rigid chassis is that it provide a stable base for all the surgical arms so that they may be accurately and precisely kinematically positioned and tracked by the surgical robotic controller in a single surgical robotic coordinate space.

The chassis 12 of the robotic surgical system 10 can be configured to be temporarily placed under a surgical table 40 when performing the robotic surgical procedure, allowing the robotic surgical system 10 to be stored remotely before and after the procedure. The robotic arms 20, 22, and 24 may optionally be configured to be retracted into the chassis 12 of the robotic surgical system, allowing the system to be moved into or out of the surgical field in a compact configuration. The first and second robotic arms 20 and 22 are shown to hold tool holders 26 and 28, as described for example in commonly owned PCT application no. PCT/EP2024/068766, filed Jul. 3, 2024, the full disclosure of which is incorporated herein by reference. The first and second robotic arms 20 and 22 could be configured to hold tool grippers, such as those described in U.S. patent application Ser. No. 18/631,921, the full disclosure of which is incorporated herein by reference, or any one of a variety of robotic surgical tools known in the art. The chassis 12 will typically be mounted on wheels 42, casters, rollers, or the like, to allow repositioning the cassis within the operating room and/or beneath the surgical table 40.

The surgical table 40 can comprise a mobile frame 42 having support columns 44 at the head and foot ends of the table (only the support column at the foot end is visible in FIG. 1). A patient bed 46 for supporting draped patient P can span the axial length of the surgical table 40 and be attached to the support columns 44 by bed adjustment mechanisms 48. The support columns 44 can be vertically adjustable allowing the height of each end of the patient bed 46 to be independently changed, and the bed adjustment mechanism 48 can allow the patient bed 46 to be reoriented about one or several axes.

While the exemplary mobile chassis 12 shown in FIG. 1 can be deployed beneath a surgical table 40, the disclosed technologies can also be incorporated into non-mobile surgical robots, such as those incorporated into a surgical table frame, as well as mobile surgical robotic carts and chasses which are not configured to extend beneath a surgical table. For example, surgical robotic carts and chasses incorporating the disclosed technologies can be configured to be deployed adjacent to a side, head, and/or foot of a surgical bed.

Figure 2:
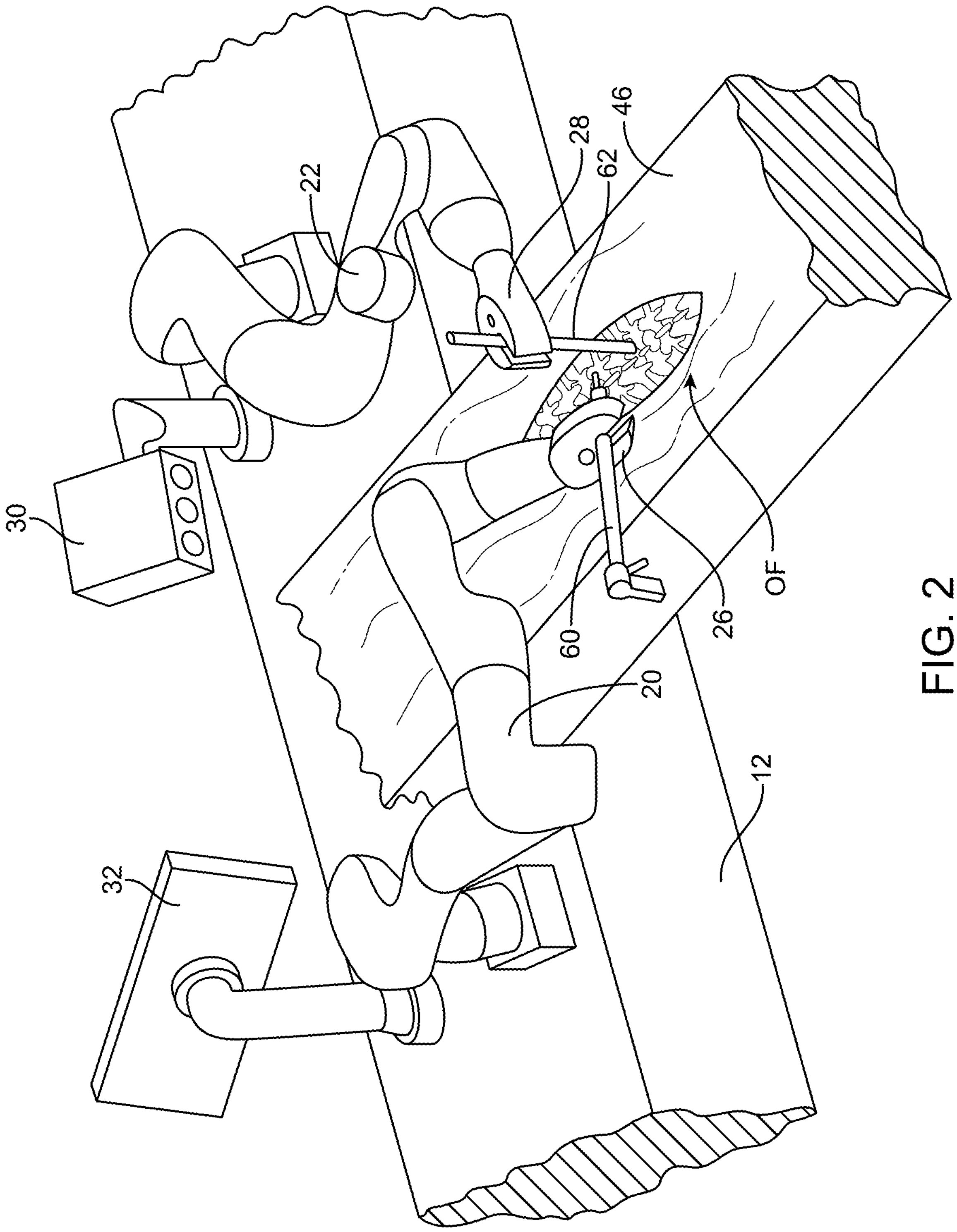
FIG. 2 is a close-up perspective view of the mobile surgical robotic cart of the FIG. 1 shown with first and second surgical robotic arms positioned over a surgically exposed portion of the patient's spine, in accordance with some embodiments.

As shown for example in FIG. 2, the surgical robotic methods and systems of the disclosed technologies can employ at least first and second surgical arms 20 and 22 which carry first and second tool holders 26 and 28, respectively. The tool holders 26 and 28, in turn, can carry a first surgical tool 60 and a second surgical tool 62. The tools 60 and 62 may be any one of numerous different types of interventional surgical tools, including drills, grinders, distractors, screws drivers, and implant insertion tools, as well as being a cannula, sheath, or the like, configured to position such interventional tools. The first surgical tool 60 is illustrated as a surgical drill having a shaft which is grasped directly in the tool holder 26 while the second surgical tool 62 is illustrated as a cannula or other tubular surgical tool suitable for positioning an interventional surgical tool.

Figure 3A:
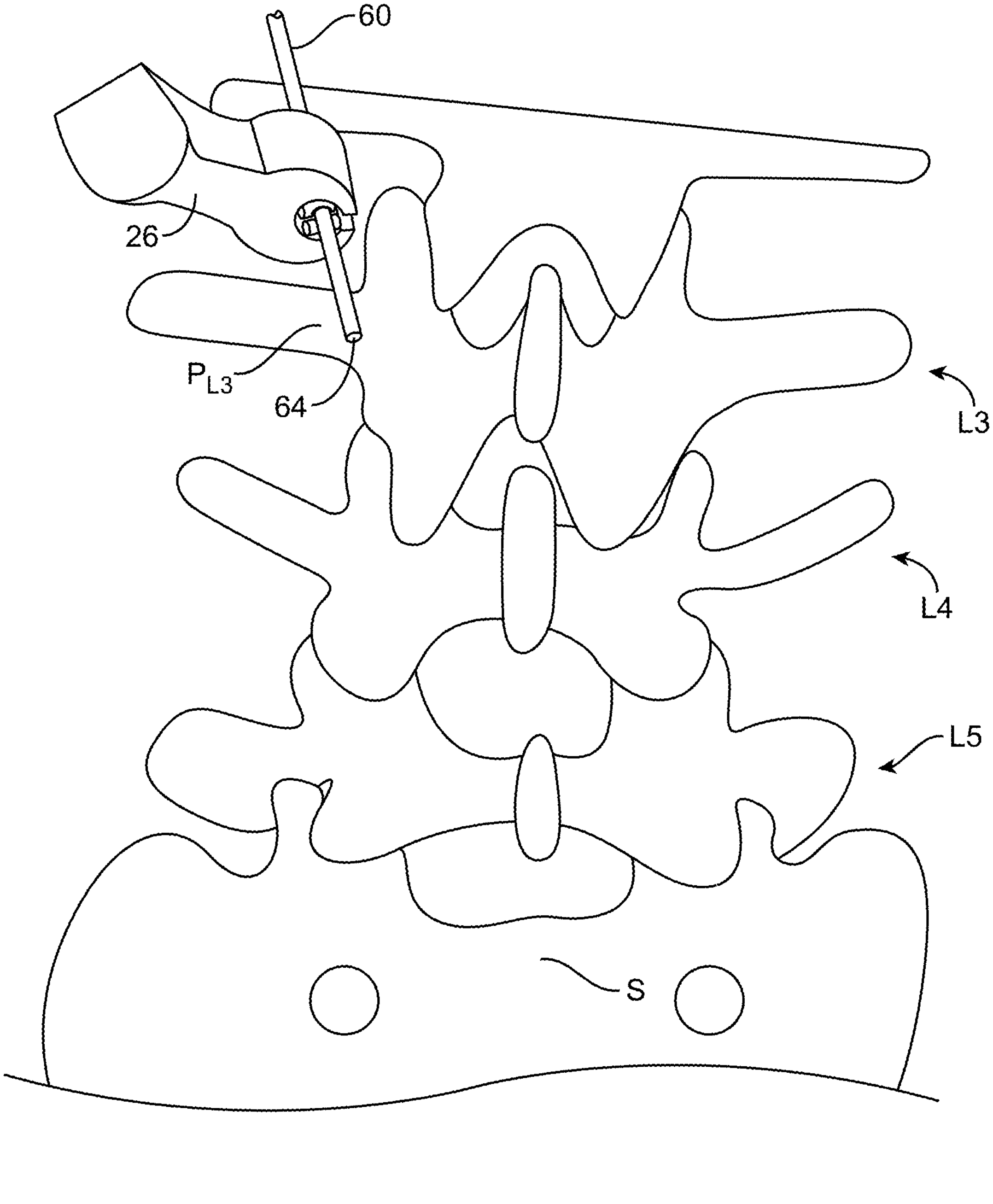
FIGS. 3A, 3B, 3C, 3D, 3E, and 3F illustrate the use of the surgical robotic system of FIGS. 1 and 2 for performing a stabilized orthopedic procedure using two robotic surgical arms, in accordance with the disclosed technologies.
Figure 3B:
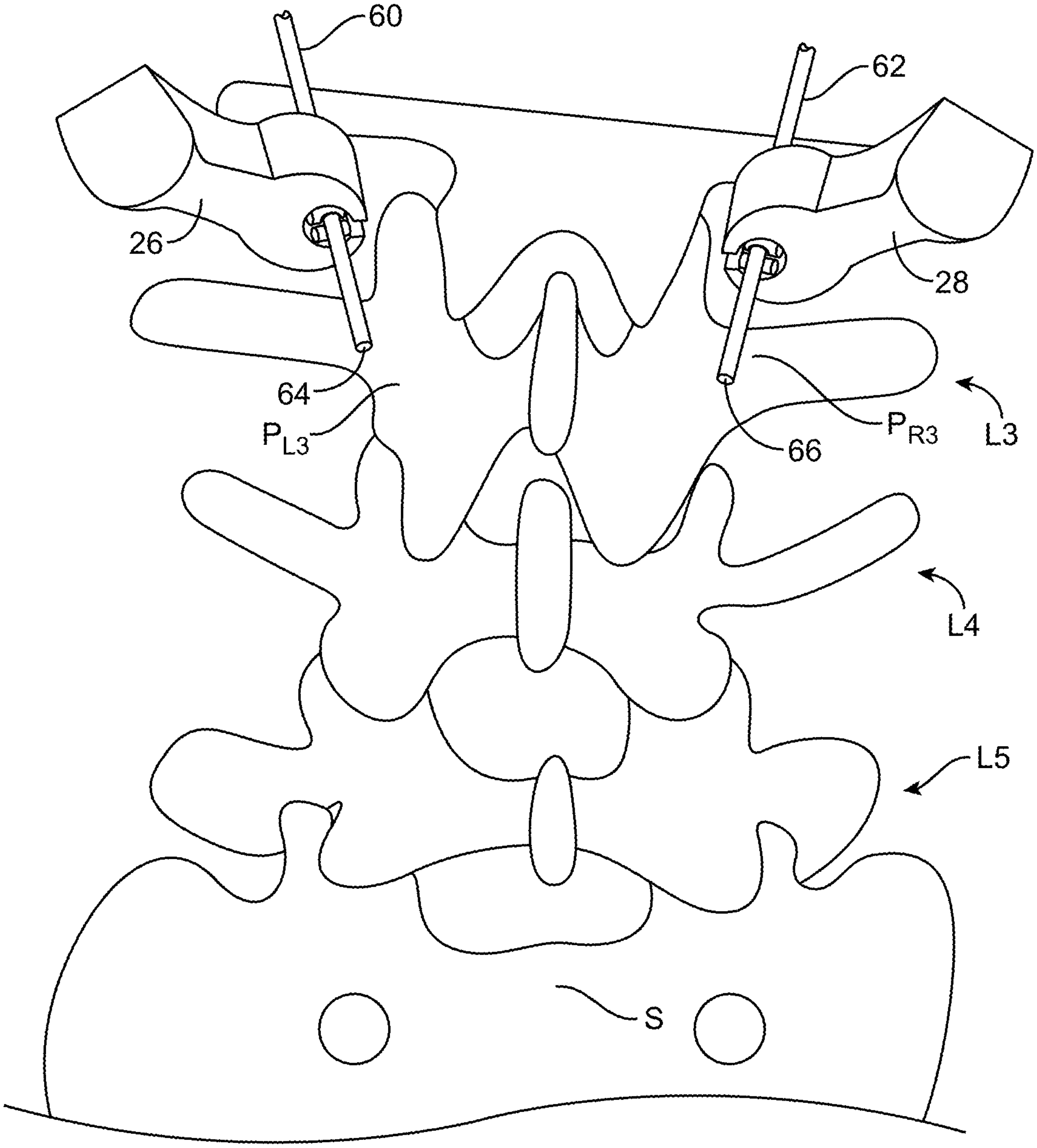

Referring now to FIGS. 3A to 3F, the use of first and second robotic surgical tools 60 and 62 for providing anatomical stabilization during a procedure on a patient's lumbar spine will be described. As shown in FIG. 3A, the first tool holder 26 can be robotically manipulated to position a distal tip 64 of the first tool 60 at a target region on the patient's left pedicle region $P_{L3}$ on L3. The first surgical tool 60 can be a surgical drill and can be used to drill a hole for subsequent placement of a pedicle screw a using screwdriver-pedicle screw assembly (not shown) in a conventional manner. The screwdriver-pedicle screw assembly can be exchanged for drill and manipulated by the same tool holder 26 and surgical robotic arm 20 or can be manipulated by a different surgical robotic arm. Regardless of the specific steps employed, once the pedicle screw is implanted in the pedicle region $P_{L3}$, the pedicle screw can remain attached to the screwdriver, and the supporting surgical robotic arm can be immobilized to stabilize the L3 vertebra, while a surgical drill and screwdriver, shown schematically as 62 in FIG. 3B, are operated to implant a pedicle screw on the patient's right pedicle region $P_{R3}$ on L3.

After implanting the second pedicle screw or other implant in the patient's right pedicle region $P_{R3}$ on L3, as shown schematically in FIG. 3B, the pedicle screw implanted by tool 60 in the patient's left pedicle region $P_{L3}$ on L3 can be released and the tool holder 26 be repositioned. The tool 60 (schematically representing both a drill and screwdriver-screw assembly which would be used in sequence) can be used to drill and implant a pedicle screw in the patient's left pedicle region $P_{L4}$ on L4 as shown schematically in FIG. 3C. The screwdriver-pedicle screw represented by tool 62 can remain immobilized in $P_{R3}$ to help stabilize L4. While the stabilizing effect will not be as great as when the stabilizing and drilling tools are acting on the same vertebra, the effect will still be significant.

Figure 3C:
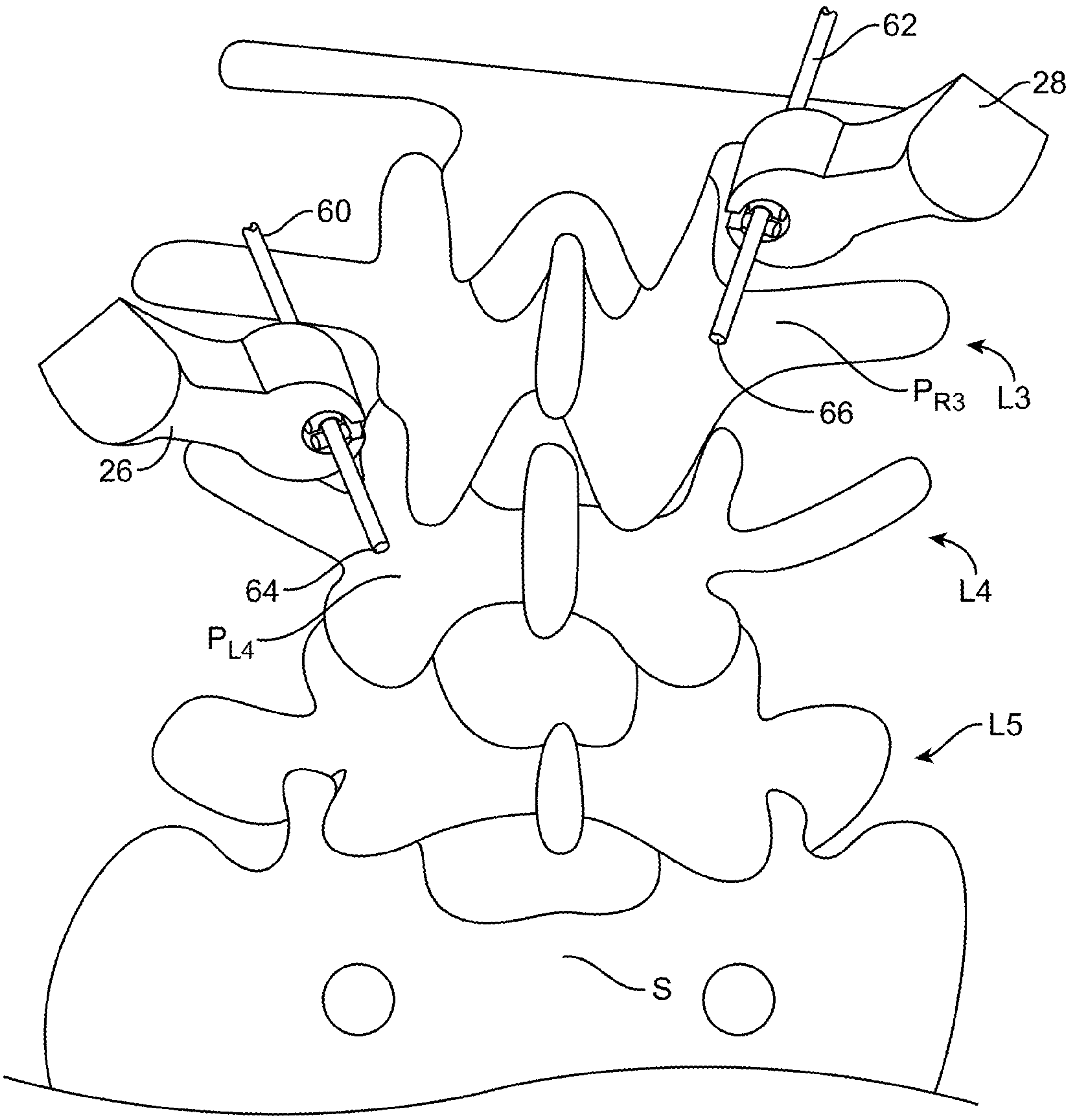
Figure 3D:
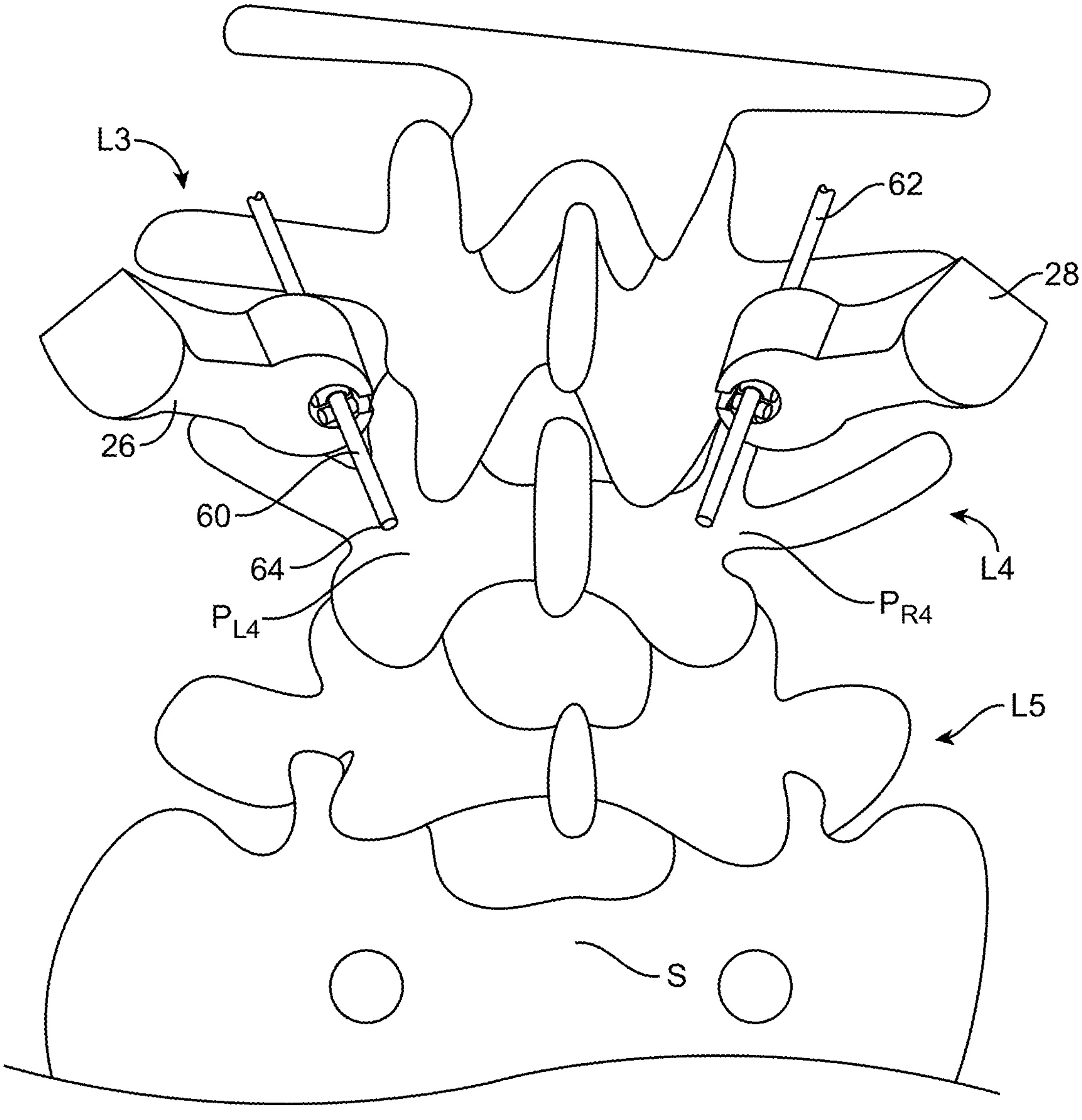

After implanting the third pedicle screw or other implant in the patient's left pedicle region PLA on L4, as shown schematically in FIG. 3C, the pedicle screw implanted by tool 62 in the patient's right pedicle region $P_{R3}$ on L3 can be released and the tool holder 28 be repositioned and used to drill and implant a pedicle screw in the patient's right pedicle region $P_{r4}$ on L4 as shown schematically in FIG. 3D. The screwdriver-pedicle screw represented by tool 60 can remain immobilized in $P_{L4}$ to stabilize L4 during drilling and screw implantation on the right side of L4.

Figure 3E:
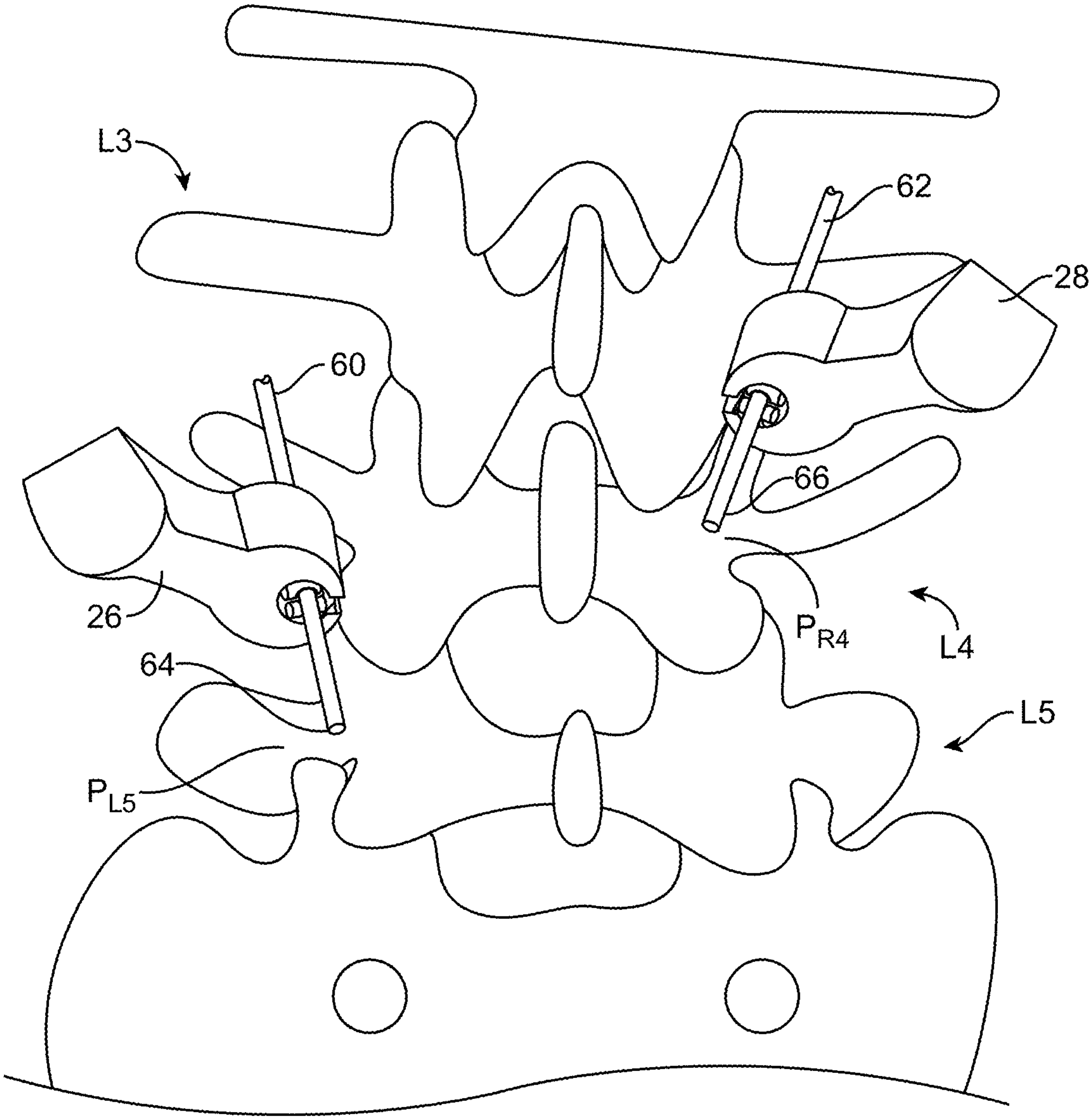
Figure 3F:
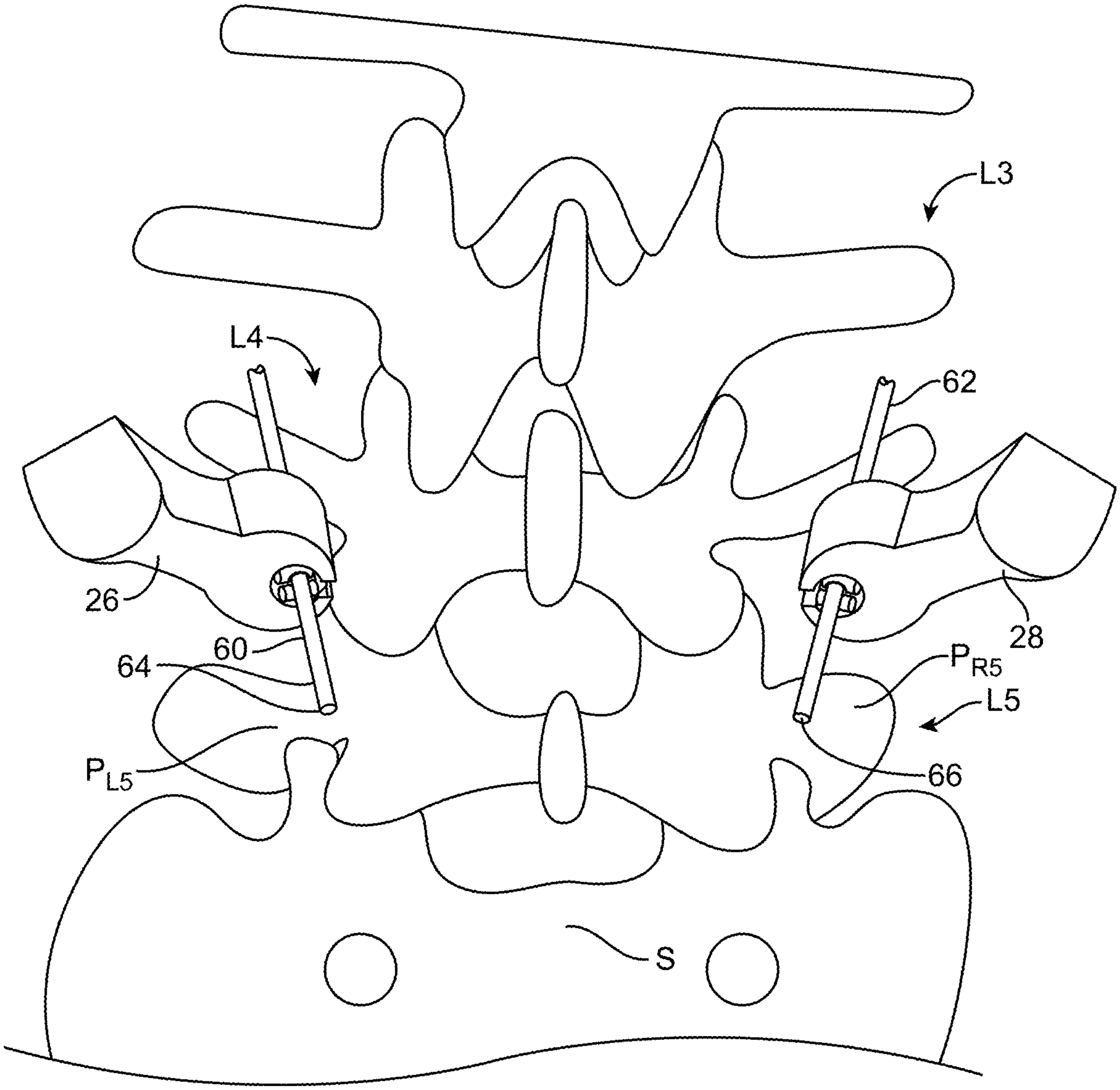

The sequential immobilization and implantation steps can be repeated in a zigzag pattern as shown on L5 as shown in FIGS. 3E and 3F and, once completed, the pedicle screws can be attached to rods in a conventional fashion.

While it will usually be preferred to immobilize the bony anatomy with a tool or implant that penetrates the anatomy, in some cases such penetration may not be necessary or even possible. In such cases, a non-penetrating engagement can be used to provide stabilization of the bony anatomy. For example, prior to drilling and implanting a first pedicle screw, as shown in FIG. 3A, tool 62 manipulated by robotic surgical arm 22 can be located to engage but not penetrate the right pedicle region $P_{R3}$ or some other surface of L3. Such non-penetrating stabilization can be particularly useful when performing the first drilling or implantation in a series of such steps.

Figure 4:
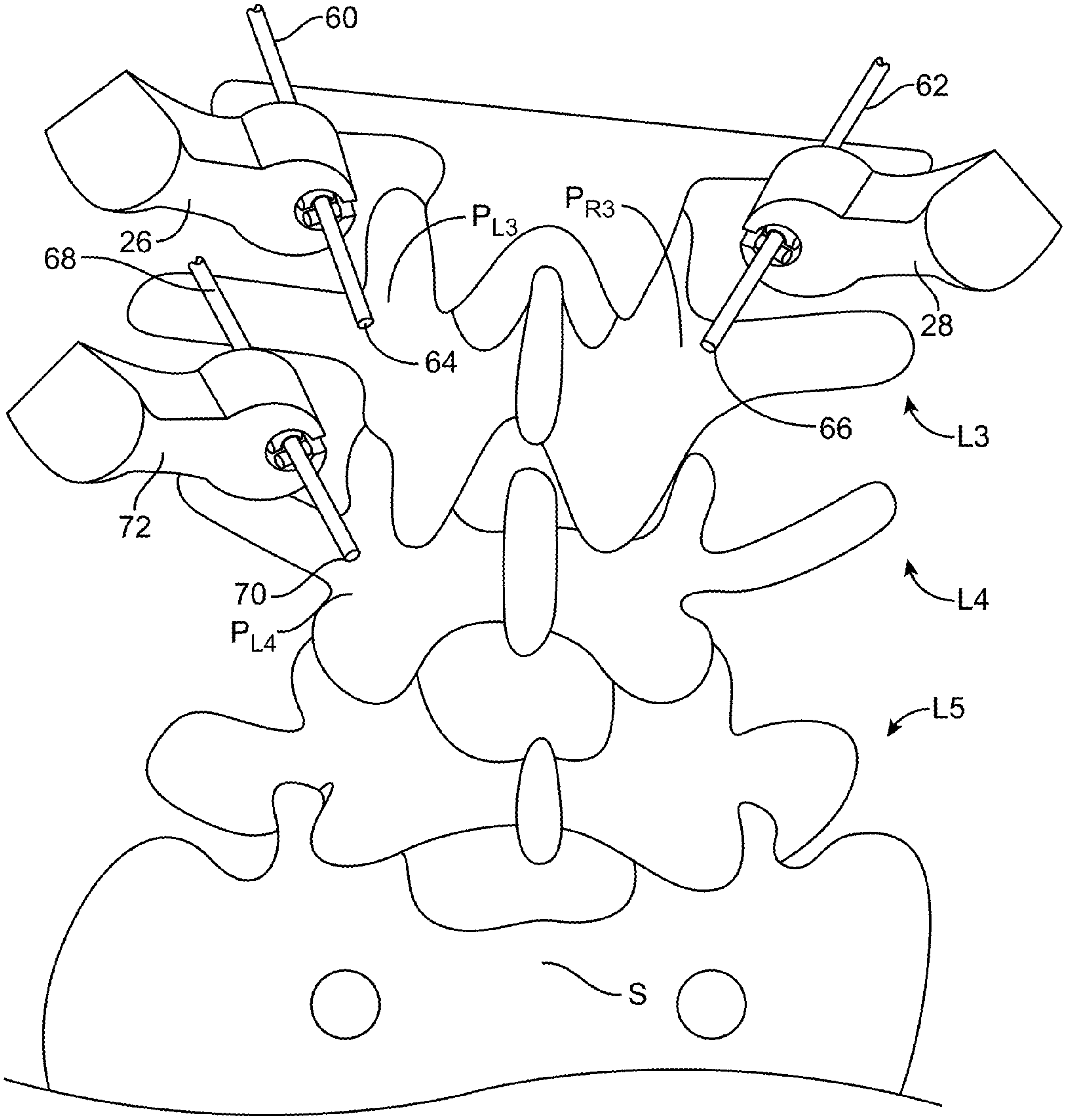
FIG. 4 illustrate the use of a surgical robotic system having three surgical robotic arms carrying three surgical tools for performing a stabilized orthopedic procedure, in accordance with the disclosed technologies.

Referring now to FIG. 4, while the methods of the disclosed technology can be performed using only two surgical arms 20 and 22 and two tool holders 26 and 28, in some instances three, four or even more surgical arm and tool combinations can be used to provide additional stabilization and/or additional operative capabilities. For example, a third surgical tool 68 having a distal tip 70 can be carried by a third tool holder 72 which can be used while the first and second tool combination 60 and 62 remain attached to or otherwise engaged with the bony anatomy to stabilize L3. In other instances, the third tool 68 can be used to provide addition stability with either or both of tools 60 and 62 being used to perform an interventional step.

| Reference Nos. | |
|---|---|
| 10 | Robotic surgical system |
| 12 | Chassis |
| 14 | First end |
| 16 | Second end |
| 18 | Upper surface |
| 20 | Robotic surgical arm (first) |
| 22 | Robotic surgical arm (second) |
| 24 | Robotic surgical arm (third) |
| 26 | First tool holder |
| 28 | Second tool holder |
| 30 | Navigation camera |
| 32 | Display/Controller |
| 34 | Wheel |
| 40 | Surgical table |
| 42 | Mobile frame |
| 44 | Support column |
| 46 | Patient bed |
| 48 | Bed adjustment mechanism |
| 60 | First surgical tool |
| 62 | Second surgical tool |
| 64 | Distal tip of first surgical tool |
| 66 | Distal tip of second surgical tool |
| 68 | Third surgical tool |
| 70 | Distal tip of third surgical tool |
| 72 | Third tool holder |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. One of skill in the art will realize that several variations on the disclosed embodiments are possible while staying within the bounds of the described technology. Solely by way of example, different variations in the number of navigation cameras, robotic arms, markers and end effectors can be used without departing from the described technology. As another example, markers of varying sizes can be used. The embodiments provided are representative in nature.

What is claimed is:

1. A robotic method for performing successive robotic surgical procedures on a patient's bony anatomy, the method comprising:

engaging a first location in the patient's bony anatomy with a first tool coupled to a first surgical robotic arm;

operating the first tool to perform a first procedure at the first location;

engaging a second location spaced apart from the first location in the patient's bony anatomy with a second tool coupled to a second surgical robotic arm; and operating the second tool to perform a second procedure at the second location after the first procedure has been completed and operating the first tool has stopped;

wherein the first surgical robotic arm and the first tool and/or a first implant attached to the first tool remain engaged with the first location on the patient's bony anatomy to stabilize the bony anatomy while the second procedure is being performed with the second surgical robotic arm and the second tool at the second location.

2. The robotic method of claim 1, wherein the first surgical procedure penetrates the first tool and/or implant into the bony anatomy and wherein the first tool and/or implant remains penetrated in the patient's bony anatomy to stabilize the bony anatomy while the second procedure is being performed.

3. The robotic method of claim 1, wherein the first procedure comprises drilling.

4. The robotic method of claim 3, wherein the first procedure further comprises placing an implant.

5. The robotic method of claim 4, wherein the first procedure comprises drilling and placing a first pedicle screw at a first location in the patient's bony anatomy.

6. The robotic method of claim 5, wherein second procedure comprises drilling and placing a second pedicle screw at a second location in the patient's bony anatomy.

7. The robotic method of claim 6, wherein the first and second locations are in the same vertebra.

8. The robotic method of claim 6, wherein the first and second locations are in separate vertebra.

9. The robotic method of claim 5, further comprising placing additional pedicle screws in a zig-zag pattern while alternating stabilization with the first and second robotic arms.

10. A robotic method for successively placing implants into a patient's bony anatomy, the method comprising:

drilling a hole at a first location in the bony anatomy with a drill held by a first robotic arm;

screwing a first pedicle screw in the drilled hole with a screwdriver held by the first surgical robotic arm; and placing a second implant at a second location spaced apart from the first location in the bony anatomy with one or more tools held by a second surgical robotic arm after the first pedicle screw has been screwed in place;

wherein the first surgical robotic arm remains attached to the first pedicle screw to stabilize the bony anatomy while the second implant is being placed at the second location.

11. The robotic method of claim 10, wherein placing the second implant comprises drilling and placing a second pedicle screw at the second location.

12. The robotic method of claim 11, wherein the first and second locations are on opposite sides of the same vertebra.

13. The robotic method of claim 11, wherein the first and second locations are in successive vertebra.

14. The robotic method of claim 13, further comprising placing additional pedicle screws in a zig-zag pattern while alternating stabilization with the first and second robotic arms.

15. A robotic surgical system comprising:

a chassis;

a first surgical robotic arm disposed on the chassis and configured to hold a first surgical tool or implant;

a second surgical robotic arm disposed on the chassis and configured to hold a second surgical tool or implant; and a surgical robotic controller, wherein the surgical robotic controller is configured to control motion of the first and second surgical arms and the first and second tools or implants so that (a) the first surgical robotic arm locates the first tool or the first implant at a first anatomical location and operates the first tool to perform a first procedure on the first location on the patient's bony anatomy, (b) operation of the first tool is stopped after the first procedure is completed, and (c) the first tool or implant attached to the first tool remains engaged with the first location on the patient's bony anatomy after the first procedure is completed to stabilize the bony anatomy while a second procedure is being performed at a second anatomical location spaced apart from the first location with the second surgical robotic arm and the second tool or the second implant.

16. The robotic surgical system of claim 15, wherein the surgical robotic controller is further configured to control motion of the first arm and the first tool or implant to penetrates the first tool or implant into the bony anatomy and to cause the first tool or implant to remain penetrated in the patient's bony anatomy to stabilize the bony anatomy while the second procedure is being performed.

17. The robotic surgical system of claim 15, wherein the first procedure comprises drilling.

18. The robotic surgical system of claim 15, wherein the first procedure comprises placing an implant.

19. The robotic surgical system of claim 15, wherein the first procedure comprises drilling and placing a first pedicle screw at a first location in the patient's bony anatomy.

20. The robotic surgical system of claim 19, wherein second procedure comprises drilling and placing a second pedicle screw at a second location in the patient's bony anatomy.

21. The robotic surgical system of claim 20, wherein the first and second locations are in the same vertebra.

22. The robotic surgical system of claim 20, wherein the first and second locations are in separate vertebra.

23. The robotic surgical system of claim 20, wherein the surgical robotic controller is further configured to control motion of the first and second surgical arms and tools or implants to implant pedicle screws in a zig-zag pattern while alternating stabilization with the first and second robotic arms.

* * * * *